United States Patent [19]
Rabbett

[11] Patent Number: 5,886,247
[45] Date of Patent: Mar. 23, 1999

[54] HIGH SENSITIVITY GAS DETECTION

[75] Inventor: Michael David Rabbett, Maidenhead, England

[73] Assignee: Forney Corporation, Carrollton, Tex.

[21] Appl. No.: 874,330

[22] Filed: Jun. 13, 1997

[30] Foreign Application Priority Data

Jun. 24, 1996 [GB] United Kingdom ............... 9613174

[51] Int. Cl.⁶ .................. G01N 7/00; G01N 21/00; G01J 5/02
[52] U.S. Cl. .............. 73/23.2; 250/339.13; 356/437
[58] Field of Search ............ 73/23.2; 250/343, 250/339.13, 345; 356/437

[56] References Cited

U.S. PATENT DOCUMENTS

| | | | |
|---|---|---|---|
| 3,825,756 | 7/1974 | Weiss | 250/343 |
| 3,851,176 | 11/1974 | Jeunehomme et al. | 250/343 |
| 3,939,348 | 2/1976 | Barrett | 250/339.13 |
| 3,976,883 | 8/1976 | Krakow | 250/343 |
| 4,035,643 | 7/1977 | Barrett | 250/339.13 |
| 4,676,642 | 6/1987 | French | 356/346 |
| 4,692,621 | 9/1987 | Passaro et al. | 250/343 |
| 4,839,614 | 6/1989 | Hill et al. | 359/238 |
| 4,998,017 | 3/1991 | Ryan et al. | 250/343 |
| 5,070,245 | 12/1991 | Rantala et al. | 250/343 |
| 5,076,699 | 12/1991 | Ryan et al. | 356/437 |
| 5,162,658 | 11/1992 | Turner et al. | 250/554 |
| 5,218,422 | 6/1993 | Zoechbauer | 356/352 |
| 5,225,888 | 7/1993 | Selwyn et al. | 356/409 |
| 5,506,685 | 4/1996 | Grasdepot | 356/409 |

FOREIGN PATENT DOCUMENTS

| | | | |
|---|---|---|---|
| 0 396 319 | 7/1990 | European Pat. Off. | G01N 21/45 |
| 1 510 521 | 5/1978 | United Kingdom | G01J 3/26 |
| 2 215 039 | 9/1989 | United Kingdom | G01N 21/25 |
| 2 286 041 | 8/1995 | United Kingdom | G01N 21/35 |
| WO 93/09422 | 5/1993 | WIPO | G01N 21/35 |

Primary Examiner—Hezron Williams
Assistant Examiner—Jay L. Politzer
Attorney, Agent, or Firm—Lane, Aitken & McCann

[57] ABSTRACT

Apparatus and a method for detecting the presence of a predetermined target gas (e.g. CO) is disclosed. The gas has a predetermined pattern of peaks of absorbance to radiation lying within a particular radiation range (e.g. infrared), the absorbance peaks alternating with gaps in which the gas transmits the radiation. A source (12) passes IR radiation through a comb filter (5) and a measurement cell (22) containing the target gas. The comb filter (5) has successive passbands separated by absorbance gaps. The passbands of the comb filter are repeatedly shifted relative to the IR radiation between a correlation position in which they coincide with at least some of the absorbance peaks of the target gas and an anti-correlation position in which the passbands coincide with at least some of the absorbance gaps of the gas. A detector (26) produces a measurement output corresponding to the radiation received through the cell (22) as the comb filter (5) is moved between the correlation and anti-correlation positions, the measurement output being a function of the presence of the target gas in the measurement cell (22). The comb filter is scanned smoothly and continuously between the two positions and the outputs corresponding to predetermined points in each scan may be accumulated over a period to increase the signal to noise ratio. A reference cell (20) receives some of the radiation passing through the comb filter (5) and contains a predetermined gas which may be the target gas. The output of the reference cell is detected is detected by a detector (44) and can be used to correct for drift in the comb filter (5) which may be an etalon.

32 Claims, 3 Drawing Sheets

HIGH SENSITIVITY GAS DETECTION

The invention relates to high sensitivity gas detection. Embodiments of the invention to be described in more detail, by way of example only, are for detecting carbon monoxide gas, possibly in the presence of other interfering substances. However, many other gases can also be detected.

According to the invention, there is provided a method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filter having predetermined successive sharp passbands separated by absorbance gaps; repeatedly shifting the passbands of the comb filter relative to the said radiation band over at least part of a range which includes a correlation position in which the passbands substantially coincide with at least some of the absorbance peaks of the gas and an anti-correlation position in which the passbands substantially coincide with at least some of the absorbance gaps of the said gas; and producing a measurement output corresponding to the radiation received at the end of the radiation path as the passbands of the comb filter are shifted whereby the measurement output is a function of the presence of the target gas in the measurement volume; the comb filter being shifted smoothly and continuously over at least the said part of the range.

According to the invention, there is further provided a method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filter having predetermined successive sharp passbands separated by absorbance gaps; repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; producing a measurement output corresponding to the radiation received at the end of the radiation path as the comb filter is shifted whereby the measurement output is a function of the presence of the target gas in the measurement volume; directing some, only, of the radiation in the main radiation path into a reference radiation path after the radiation in the main path has passed through the comb filter but before it has passed into the measurement volume; passing the radiation in the reference path through a reference volume containing a predetermined reference gas having a predetermined absorption characteristic; detecting the radiation after it has passed through the reference volume and producing a corresponding reference output; and using the reference output to correct the measurement output for any changes therein caused by drift in the comb filter.

According to the invention, there is also provided a method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filter having predetermined successive sharp passbands separated by absorbance gaps; repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; producing a measurement output corresponding to the radiation received at the end of the radiation path as the comb filter is shifted whereby the measurement output is a function of the presence of the target gas in the measurement volume; storing at least one predetermined reference signal whose variation corresponds to the variation in the measurement output expected in the presence of the target gas in the measurement volume; and comparing the measurement output with the stored signal whereby to determine if the measurement output corresponds to the presence of the target gas in the measurement volume.

According to the invention, there is still further provided a method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filter having predetermined successive sharp passbands separated by absorbance gaps; repeatedly shifting the passbands of the comb filter, relative to the said radiation band, over at least part of a range which includes a correlation position in which the passbands substantially coincide with at least some of the absorbance peaks of the gas and an anti-correlation position in which the passbands substantially coincide with at least some of the absorbance gaps of the said gas, the said part of the range including the correlation position; and producing a measurement output corresponding to the radiation received at the end of the radiation path as the comb filter is shifted whereby the measurement output is a function of the presence of the target gas in the measurement volume, the passbands of the comb filter when in the correlation position being aligned with some, only, of the absorbance peaks of the target gas, the excluded absorbance peaks also corresponding to the absorbance peaks of another gas.

According to the invention, there is further provided apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement volume being adapted to receive the said gas; the comb filter having predetermined successive sharp passbands separated by absorbance gaps; means for repeatedly shifting the passbands of the comb filter, relative to the said radiation band, over at least part of a range which includes a correlation position in which the passbands substantially coincide with at least some of the absorbance peaks of the gas and an anti-correlation position in which the passbands substantially coincide with at least some of the absorbance gaps of the said gas; output means for producing a measurement output corresponding to the radiation received at the end of the radiation path as the comb filter is shifted whereby the measurement output is a function of the presence of the target gas in the measurement volume; and shifting means for shifting the comb filter smoothly and continuously over at least the said part of the range.

According to the invention, there is also provided apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement volume being adapted to receive the said gas; the comb filter having predetermined successive sharp passbands separated by absorbance gaps; means for repeatedly shifting the passbands of the comb filter, relative to the said radiation band, over at least part of a range which includes a correlation position in which the passbands substantially coincide with at least some of the absorbance peaks of the gas and an anti-correlation position in which the passbands substantially coincide with at least some of the absorbance gaps of the said gas; output means for producing a measurement output corresponding to the radiation received at the end of the radiation path as the passbands of the comb filter are shifted whereby the measurement output is a function of the presence of the target gas in the measurement volume; means for directing some, only, of the radiation in the main radiation path into a reference radiation path after the radiation in the main path has passed through the comb filter but before it has passed into the measurement volume; means for passing the radiation in the reference path through a reference volume containing a predetermined reference gas having a predetermined absorption characteristic; detecting means for detecting the radiation after it has passed through the reference volume and producing a corresponding reference output; and means responsive to the reference output to correct the measurement output for any changes therein caused by drift in the comb filter.

According to the invention, there is yet further provided apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement volume being adapted to receive the gas; the comb filter having predetermined successive sharp passbands separated by absorbance gaps; means for repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; output means for producing a measurement output corresponding to the radiation received at the end of the radiation path as the passbands of the comb filter are shifted whereby the measurement output is a function of the presence of the target gas in the measurement volume; storing means for storing at least one predetermined reference signal whose variation corresponds to the variation in the measurement output expected in the presence of the target gas in the measurement volume; and comparing means for comparing the measurement output with the stored signal whereby to determine if the measurement output corresponds to the presence of the target gas in the measurement volume.

According to the invention, there is still further provided apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement value being adapted to receive the said gas; the comb filter having predetermined successive sharp passbands separated by absorbance gaps; means for repeatedly shifting the passbands of the comb filter, relative to the said radiation range, over at least part of a range including a correlation position in which the passbands substantially coincide with at least some of the absorbance peaks of the gas and an anti-correlation position in which the passbands substantially coincide with at least some of the absorbance gaps of the said gas, the said part of the range including the correlation position; and output means for producing a measurement output corresponding to the radiation received at the end of the radiation path as the passbands of the comb filter are shifted whereby the measurement output is a function of the presence of the target gas in the measurement volume, the passbands of the comb filter when in the correlation position being aligned with some, only, of the absorbance peaks of the target gas, the excluded absorbance peaks also corresponding to the absorbance peaks of another gas.

High sensitivity gas detection apparatus and methods according to the invention will now be described, by way of example only, with reference to the accompanying diagrammatic drawings in which.

The apparatus and methods to be described are for detecting concentrations of carbon monoxide (CO) in air using infrared absorption techniques. The apparatus and methods aim to detect minimum concentrations of CO of 100 ppbv or better, possibly in the presence of interfering substances such as water and carbon dioxide. As will be explained, though, the apparatus and methods can also be used for the detection of other gases such as methane, ammonia, water vapour, hydrogen sulphide and the hydrogen halides. The apparatus and methods may also be modified to operate using ultra-violet absorption techniques.

Figure 1:
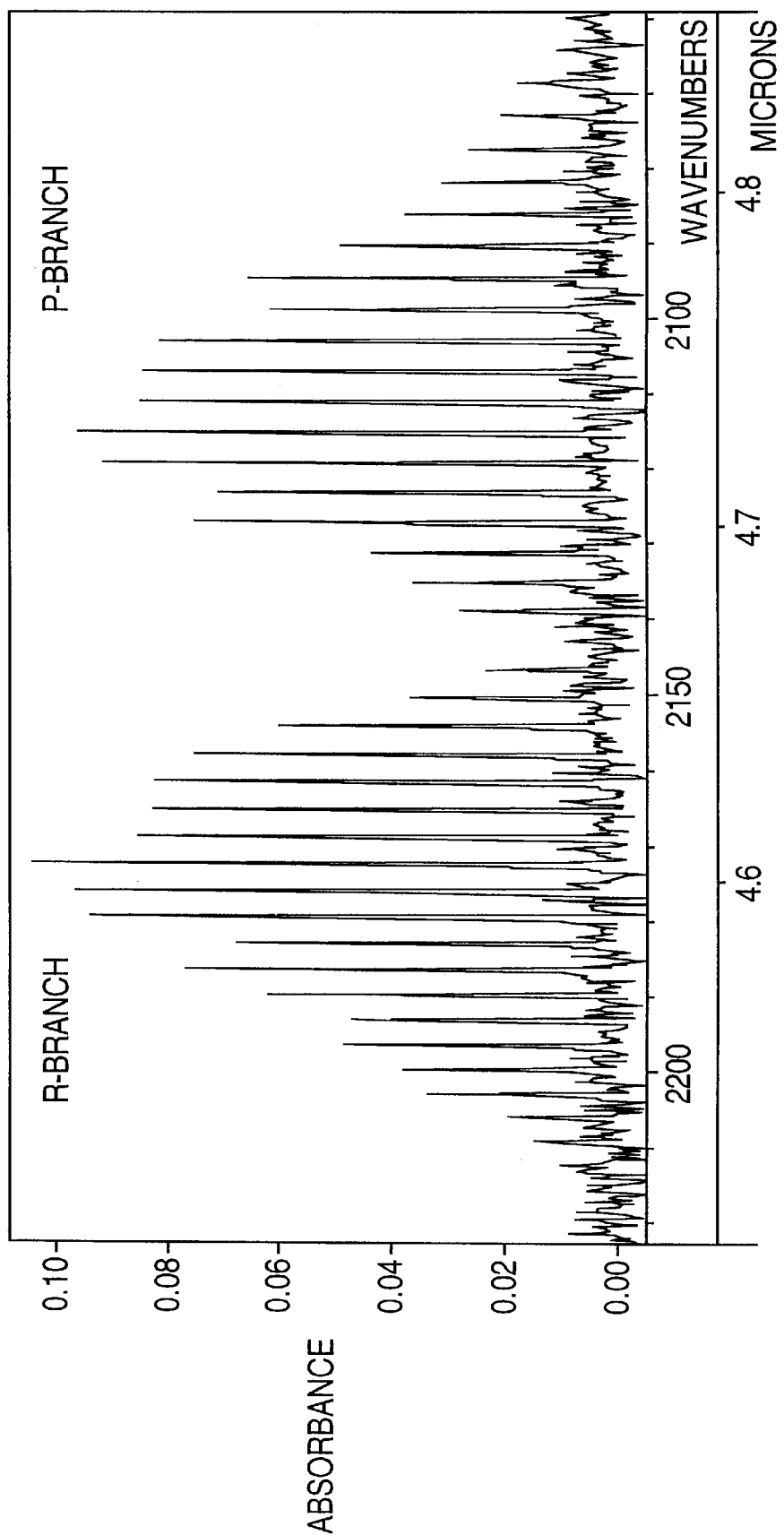
FIG. 1 is a graph showing a spectrum of absorbance bands of carbon monoxide gas.

FIG. 1 shows the absorbance characteristic or spectrum of carbon monoxide in the infrared region. As shown, the absorbance spectrum comprises a range of very narrow absorbance bands separated by regions of low or substantially zero absorption. The apparatus and methods to be described use a source which directs infrared radiation along a predetermined optical path to a detector. A comb filter and a measurement cell are placed in series in the optical path. The measurement cell contains the gas (the "target gas") to be analysed, which in this example is assumed to be a low concentration of carbon monoxide in air. The infrared radiation passes along the optical path, through the comb filter and the measurement cell to a detector. The passbands of the comb filter have the same spacing as the absorbance peaks of CO. If the passbands are aligned with the absorbance peaks, it will be apparent that the infrared radiation in the optical path will be attenuated by absorption by any carbon monoxide in the cell, and the detector will produce a low output. If now the comb filter is adjusted so that the passbands fall in the gaps between the absorbance peaks of carbon monoxide, the infrared radiation in the optical path will no longer be absorbed by the carbon monoxide. Therefore, if the comb filter is switched between the two positions, it will be apparent that an AC signal will be produced by the detector only in the presence of the target gas.

Figure 2D:
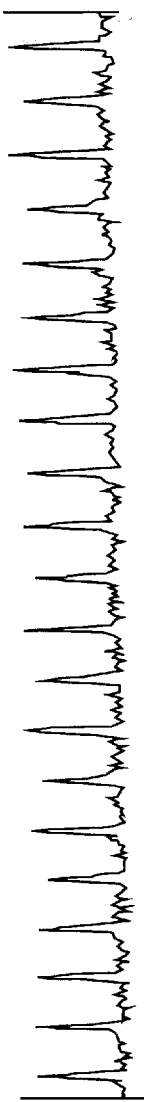
FIG. 2 shows graphs of the absorbance of carbon monoxide and of the passbands of comb filters used in the apparatus.
Figure 2C:
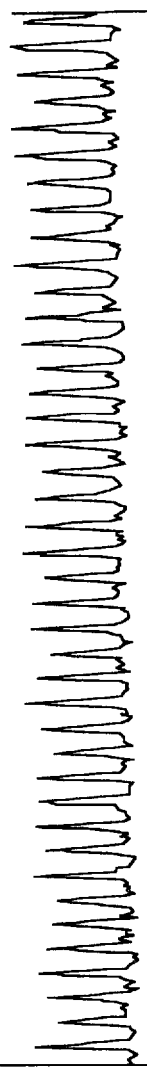
Figure 2B:
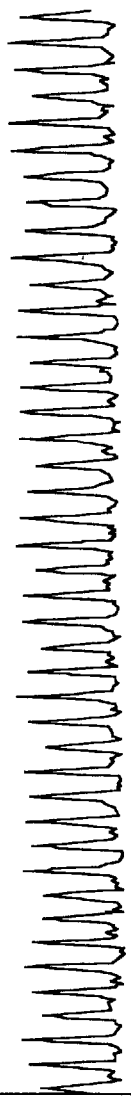
Figure 2A:
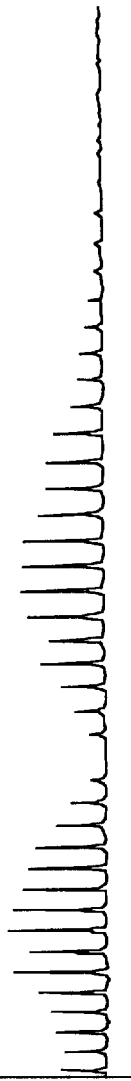

The foregoing is illustrated in FIGS. 2A and 2B. FIG. 2A shows the absorbance spectrum of carbon monoxide and thus repeats FIG. 1 to a different scale. FIG. 2B shows the passbands of a suitable comb filter, the spacing between the passbands corresponding to the spacings between the absorbance peaks of the carbon monoxide. In FIG. 2B, the comb filter is adjusted so that its passbands (or at least some of them) are aligned or substantially aligned with the absorbance peaks of the carbon monoxide (the "correlation position"). In FIG. 2C, however, the comb filter is adjusted so that its passbands (or at least some of them) are aligned or substantially aligned with the gaps between the absorbance peaks of the carbon monoxide (the "anti correlation position").

It may not be necessary to shift the comb filter over the full range between the correlation position and the anti-correlation position. Furthermore, and as stated above, not all the passbands need to be aligned, or exactly aligned, with the peaks or gaps (respectively) in the correlation and anti-correlation positions. This is because it is not only the position of the peaks which is significant but also their shapes. Thus, because the shapes are significant, a meaningful output can be achieved even when the passbands do not exactly coincide with the absorbance peaks or gaps. It may also be useful to select the limits of the scans so that a peak due to some gas other than the target gas is excluded. For example, it may be desirable when carbon monoxide is the target gas to arrange for the scan to exclude a peak due to water absorption which could otherwise produce a large output which could overload the detection process and reduce its sensitivity.

Various possible implementations can be used for the comb filter. For example, a Mach-zehnder or Michelson interferometer can he used. A more suitable type of interferometer is a Fabry-Perot interferometer (also known as a Fabry-Perot etalon) which produces a comb having much narrower passbands or "teeth". Such an etalon consists of two high quality reflectors separated by an optical space. When radiation is incident upon the etalon along its optical axis, the radiation passes into the etalon and interference occurs between radiation which has experienced successive round trips between the two reflectors. This interference leads to the desired spectral transmission profile of a series of widely spaced, very narrow teeth. The spacing between the teeth is determined by the optical thickness between the reflectors while the width of the teeth is determined by the quality of the reflectors and the divergence angle of the incident radiation; the latter factors also affect the difference in transmission at the peak of each tooth and in each trough between successive teeth.

Another possible type of comb filter is a bi-refringent filter, such as filters of the Lyot or Solc type.

In the apparatus to be described, though, an etalon is primarily used in order to implement the comb filter. The etalon is switched or scanned over at least part of a range including the correlation position and the anti-correlation position by changing the spacing between the two mirrors of the etalon slightly, about a mean spacing. As the spacing is increased very slightly with reference to the mean position, the cumulative effect of each such small increase in spacing between successive teeth within an initial range will shift all the remaining teeth so that the comb filter moves from the correlation position to the anti-correlation position (or vice versa), the change in spacing between any two adjacent teeth being insignificant compared both with the mean spacing and with the spacing between adjacent absorbance peaks of carbon monoxide. Clearly, a slight decrease in the spacing between the mirrors of the etalon similarly shifts the comb filter in the opposite direction.

Various methods may be adopted for varying the spacing between the two mirrors of the etalon. For example, piezo-electric actuators may be used to adjust the spacing. In one example, the spacing is adjusted by 2 $\mu$m about a mean value, by means of an applied voltage on the actuators, the change in spacing being proportional to the applied voltage. A DC signal applied to the actuators establishes the mean spacing.

In another example, a "solid" etalon may be used, comprising a polished piece of optical material with mirrors coated onto its two opposite faces. In this case, the etalon can be scanned between its two positions by applying changes in temperature about a mean value, so as to expand and contract the optical material. A preferred alternative, though, is to tilt the etalon in opposite angular directions about a mean tilt position so as to produce the required slight alteration in path length. Again, a piezo-electric actuator can be used for example, or a galvo-mirror scanner.

In accordance with a feature of the invention, the etalon is scanned between its two positions smoothly, preferably sinusoidally.

The apparatus will now be described in more detail with reference to FIG. 3.

Figure 3:
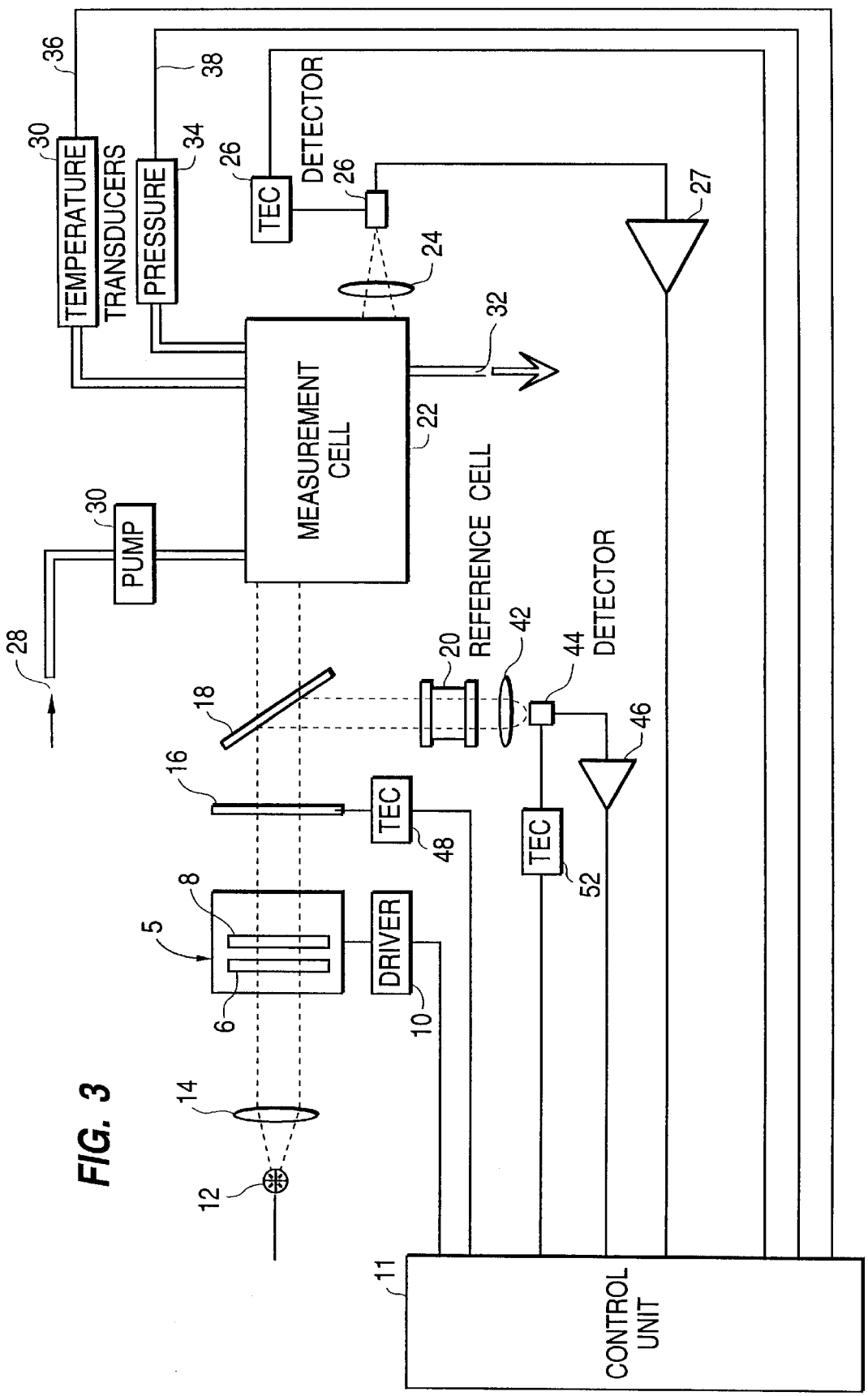
FIG. 3 is a schematic block diagram of one form of the apparatus.

FIG. 3 shows the etalon diagrammatically at 5, its two mirrors being shown at 6 and 8. A driver unit 10 applies a signal to a piezoelectric actuator (not shown) which alters the spacing between the mirrors 6,8. The driver 10 is controlled by a control unit 11. A source 12 at the infrared radiation inputs infrared radiation into the optical path through a collimating lens 14 whence it passes through the etalon and through a filter 16 to a partially transmitting mirror 18. The mirror 18 splits off a fraction of the infrared radiation to a reference cell 20 for a purpose to be described. The radiation not split off by the mirror 18 then passes through a measurement cell 22 containing the atmosphere to be analysed. The measurement cell 22 preferably contains a relatively long folded path, and the radiation exits from the cell through a lens 24 to an infrared radiation detector 26. The resultant detector output is fed through an amplifier 27 to the control unit 11. The atmosphere to be tested is drawn in to the cell 22 from an inlet 28 by a pump 30 and exits to exhaust as shown at 32. Transducers 32 and 34 measure the temperature and pressure, respectively, within the cell 22. Corresponding signals are fed on lines 36 and 38 to the control unit 11.

The reference cell 20 contains a reference gas. In one example, to be discussed in more detail below, air containing some water vapour is used. Other possibilities will also be discussed. The radiation split off by the mirror 18 passes through the reference cell and a lens 42 to an infrared radiation detector 44. The detector output is fed through an amplifier 46 to the control unit 11.

Various elements in the apparatus may be cooled by thermo-electric coolers ("TECs") 48,50 and 52 to increase their sensitivity and performance.

In operation, and as already briefly described, the driver 10 continually adjusts the spacing between the mirrors 6 and 8 over at least part of the range including the correlation and the anti-correlation positions, and the detector 26 measures the resultant infrared radiation which it receives. If the detector produces an alternating signal having at least the same periodicity as the variation of the spacing between the mirrors 6 and 8, this indicates the presence of the target gas (the target gas being the gas whose absorbance peaks have the same "pitch" as the teeth of the etalon and being assumed to be carbon monoxide in this example).

In accordance with a feature of the invention, the output of detector 26 is digitised in the control unit 11 at predetermined points in each sinusoidal scan of the etalon and the signals from the same point in successive scans are accumulated. Over a short time interval (e.g. a few seconds), this increases the level of the detector output due to the carbon monoxide and suppresses noise signals. This digitisation process may involve high frequency modulation of the etalon and the necessity to digitise the detector output signal at a few hundred points during each etalon scan. This may lead to the need to carry out more than 100,000 digitisations and signal additions per second. An alternative approach, requiring less complex electronics, involves use of a high frequency modulated radiation source 12. The output of detector 26 would of course be correspondingly modulated. A lock-in amplifier arrangement (involving relatively simple analogue components) could be used to convert the modulated output to a DC signal and filter out the detector noise. Thus, the lock-in amplifier would have a reference input derived from the modulator (and at the same frequency) and a signal input derived from the detector output. The etalon 5 is scanned relatively slowly and the output of the amplifier digitised and stored. The result is a stored spectrum as before but the complexity of the processing components has been greatly reduced. The lock-in amplifier could alternatively be implemented in software using a digital signal processing chip.

In practice, the range over which the etalon is scanned is likely to include the correlation position but, as stated above, it need not include the anti-correlation position. Desirably, the scan is arranged so that the peaks of the CO absorbance coincide with the point where the etalon passbands are changing most rapidly (within the sinusoidal scan).

One purpose of the reference cell 20 and the reference detector 44 is to take account of, and correct for, inevitable changes in the behaviour of the etalon 5. For example, temperature changes and creep of mechanical parts can change the parallelism of the mirrors 6 and 8 and the mean length of the optical spacing. If the etalon 5 is of the solid type, its mean spacing will be changed by temperature changes. Although the etalon could be temperature-stabilised, this would be complex and expensive—and would not, of course, take account of mechanical effects, particularly on types of etalon using separate parallel mirrors. The reference cell 20 operates by using a gas containing an absorber having a sharp absorbance within the band of the infrared radiation used; as described above, one possibility is to use air containing water vapour. As the etalon is scanned over its range (with respect to the carbon monoxide), the reference detector 44 will detect a signal produced by the radiation split off by the mirror 18 and passing through the reference cell 20. The strength of this signal will depend on the degree to which the mirrors 6,8 of the etalon are parallel: the largest signal will be generated when the mirrors are perfectly parallel which both maximises the radiation transmission of the etalon and minimises the width of each tooth of the etalon. Therefore, the control unit 11 measures the strength of the signal produced by the reference detector 44 and adjusts the parallelism between the mirrors 6 and 8 to maximise this signal. The parallelism between the mirrors is adjusted by means of driver 10 and piezoelectric actuators controlling the mutual position of the mirrors.

In order to detect any changes in the mean spacing of the mirrors and to correct for them, the output of the reference detector 44 is compared with a reference spectrum which has been previously generated when the mean etalon spacing is correct and stored in the control unit 40. Any change in the mean spacing of the etalon will reduce the degree of correlation between the output of the reference detector 44 and the stored reference spectrum. A suitable correction can then be made to the mean etalon spacing by the control unit, using the driver 10. The driver either alters the DC signal applied to the piezoelectric actuator which adjusts the mirror spacing or the DC signal applied to the piezoelectric actuator controlling the degree of tilt of the etalon 5 if it is of the solid form.

In a modification, the output from the reference detector 44 is not used to carry out physical adjustments on the etalon 5. Instead, the output from the reference detector 44 is compared with a stored reference spectrum, representing the output produced by the reference detector when the etalon 5 has the desired physical parameters (parallel mirrors and correct mean spacing, primarily). Any differences produced by this comparison are then used to adjust the output of the measurement detector 26. In this way, any necessary correction, due to mechanical changes in the etalon 5, are carried out wholly by software instead of by physical adjustment of the etalon.

In the foregoing example, it was assumed that the reference cell contains air and water vapour. Any other suitable sample of gas could be used in the air. For example, the reference cell could be filled with the target gas (carbon monoxide in this example). However, in cases where the target gas is a corrosive or otherwise aggressive nature, it may not be practicable to use this gas in the reference detector.

If the reference cell contains the target gas, it is also possible to use the reference cell and the reference detector to improve the selectivity of the detection in the presence of other gases. In principle, the detector 26 should only produce an AC output in the presence of the target gas. However, this may not always be the case, and certain other gases may produce an output from detector 26 in the absence of the target gas. In this case, though, the shape of the detector output (its "spectrum") will not correlate with the spectrum generated in the presence of the target gas. If the reference cell 42 contains the target gas, the spectrum of the output produced by detector 26 can be compared with the spectrum produced by the reference detector 44. A correct comparison indicates that it is the target gas which is producing the output of the measurement detector 26. Lack of correlation between the spectra respectively produced by the main detector 26 and the reference detector 44 indicates the presence of another gas. For example, the spectra can be compared by making a least squares fit of one spectrum to the other; the fitting parameter is related to the concentration of the target gas.

It will be appreciated that this comparison process carried out between the two spectra has the effect that it is no longer necessary to control the mean spacing between the mirrors of the etalon 5; any change in the mean spacing of the etalon, or the parallelism of the two mirrors, will affect both the spectrum of the output produced by the measurement detector 26 and the spectrum of the output produced by the reference detector 44, and the comparison between the two spectra will thus automatically compensate for changes in the etalon.

Instead of comparing the spectrum of the output from the main detector 26 with the spectrum produced by the reference detector 44 when the reference cell contains the target gas, the spectrum from the main detector 26 can be compared with a previously stored spectrum corresponding to the target gas. In this case, though, the comparison process will no longer take account of mechanical changes in the etalon; these can be compensated by using the output of the reference detector 44 in the manner already explained. However, comparison of the output of the main detector 26 with a stored spectrum can be used to detect more than one gas—by storing a number of different spectra corresponding to different target gases and comparing the output of the main detector 26 with each of the stored spectra. This process may be used simply to measure the concentration of several different gases. Instead, or in addition, it may be used to improve the measurement accuracy relating to a particular target gas by making higher order corrections to this measurement dependant on the detected concentration of other gases.

The foregoing procedure can be used for simultaneous measurement of the concentration of carbon monoxide, water vapour and carbon dioxide, for example.

As already indicated, the presence of other gases (that is, other than the target gas) in the measurement cell 22 can cause interference problems. For example, the presence of water vapour can interfere with the measurement of carbon monoxide. It is found that absorption peaks caused by water vapour correspond to odd-numbered absorption peaks in the right hand or "P" branch of the absorption peaks for carbon monoxide (see FIG. 1). More specifically, the absorption peaks due to water coincide specifically with the seventh and thirteenth components of the "P" branch. Advantage may be taken of this fact in order to reduce the effects of water vapour on the carbon monoxide measurements. For example, FIG. 2D shows a modified form of etalon where the spacing between its teeth is twice the spacing between absorbance peaks of carbon monoxide (instead of being equal to the latter spacing as shown in FIGS. 2B and 2C). The operation of the control unit 11 is modified so that the etalon is switched between a correlation position in which the teeth of the etalon coincide with the even-numbered absorbance peaks of the carbon monoxide spectrum and an anti-correlation position in which the teeth of the etalon coincide with the spacings between the absorbance peaks (every alternate such spacing, of course). The etalon is scanned between these correlation and anti-correlation positions, and the carbon monoxide concentration is measured in the manner already explained. In this way, any effect of the water vapour on the output of detector 26 is prevented.

In addition, however, measurements are taken with the etalon scanned over at least part of a range between a correlation position in which the teeth of the etalon coincide with the odd-numbered absorbance peaks of the carbon monoxide spectrum and an anti-correlation position in which the teeth of the etalon coincide with the spacings between the absorbance peaks of the carbon monoxide spectrum (again, every other such spacing of course). Again, therefore, the apparatus measures the concentration of carbon monoxide but this measurement is now affected by the water vapour absorbance peaks represented by the seventh and thirteenth components of the "P" branch of the CO spectrum. In this way, therefore, the effect of the water vapour on the carbon monoxide measurement can be corrected for. Furthermore, it enables the concentration of the water vapour to be measured.

In the more general sense, therefore, instead of matching the teeth of the etalon exactly to the absorbance peaks of a specific gas to be detected, it may be advantageous to match the teeth to a subset of the absorbance peaks, only, in order to achieve better rejection of interference from another gas. In one specific example, it is found that detection of methane using an etalon in the manner described may be affected by interference from water vapour, and such interference can be minimised by arranging the etalon spacing to avoid absorbance peaks caused by the water vapour.

It will be appreciated that various modifications can be made to the apparatus illustrated in FIG. 3. For example, in certain circumstances it may be desirable to increase the strength of the reference signal from the reference detector 44 such as to increase its effectiveness in correcting for drift in the etalon 5. In these circumstances, the filter 16 could be re-positioned so that the radiation passing to the reference cell 20 does not first pass through the filter. For example, the filter 16 could be positioned immediately before the final lens 24.

The collimating lens 14 can be omitted in some circumstances particularly where cost is critical and/or a reduced signal to noise ratio can be tolerated.

The pump 30 can be repositioned either upstream or downstream of the cell 22.

I claim:

1. A method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within said band along a predetermined main radiation path including a comb filter and a measurement volume in which said gas may be present; the comb filter having predetermined successive sharp passbands separated by absorbance gaps, repeatedly shifting the passbands of the comb filter relative to said radiation band over at least part of a range which includes a correlation position in which the passbands substantially coincide with at least some of the absorbance peaks of the gas and an anti-correlation position in which the passbands substantially coincide with at least some of the absorbance gaps of said gas; producing a measurement output corresponding to the radiation received at the end of the radiation path as the passbands of the comb filter are shifted wherein the measurement output is a function of the presence of the target gas in the measurement volume; producing an electrical output corresponding to the radiation detected during each shift of the passbands, and summing the level of the electrical output at each of a plurality of predetermined points in each of a predetermined plurality of successive shifts with a corresponding level in the other shifts of that plurality whereby to produce an output signal in which the value dependent on the target gas is increased relative to any value due to noise.

2. A method according to claim 1, in which the comb filter is shifted sinusoidally over at least said part of the range.

3. A method according to claim 1, in which the electrical output is digitised at each of the predetermined points.

4. A method according to claim 1, in which the radiation passed along the predetermined main radiation path is modulated at high frequency to produce corresponding modulation in the measurement output, and including the step of converting the modulated measurement output to a DC signal, and digitising the DC signal at the predetermined points during the successive said shifts.

5. A method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within said band along a predetermined main radiation path including a comb filter and a measurement volume in which said gas may be present; the comb filter having predetermined successive sharp passbands separated by absorbance gaps, repeatedly shifting the passbands of the comb filter relative to said radiation band over at least part of a range which includes a correlation position in which the passbands substantially coincide with at least some of the absorbance peaks of the gas and an anti-correlation position in which the passbands substantially coincide with at least some of the absorbance gaps of said gas; producing a measurement output corresponding to the radiation received at the end of the radiation path as the passbands of the comb filter are shifted wherein the measurement output is a function of the presence of the target gas in the measurement volume; the comb filter being shifted smoothly and continuously over at least said part of the range, directing some, only, of the radiation in the main radiation path into a reference radiation path after the radiation in the main path has passed through the comb filter but before it has passed into the measurement volume, passing the radiation in the reference path through a reference volume containing a predetermined reference gas having a predetermined absorption characteristic, detecting the radiation after it has passed through the reference volume and producing a corresponding reference output, and using the reference output to correct the measurement output for any changes therein caused by drift in the comb filter.

6. A method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within said band along a predetermined main radiation path including a comb filter and a measurement volume in which said gas may be present; the comb filter having predetermined successive sharp passbands separated by absorbance gaps, repeatedly shifting the passbands of the comb filter relative to said radiation band over at least part of a range which includes a correlation position in which the passbands substantially coincide with at least some of the absorbance peaks of the gas and an anti-correlation position in which the passbands substantially coincide with at least some of the absorbance gaps of said gas; and producing a measurement output corresponding to the radiation received at the end of the radiation path as the passbands of the comb filter are shifted wherein the measurement output is a function of the presence of the target gas in the measurement volume; the comb filter being shifted smoothly and continuously over at least said part of the range, directing some, only, of the radiation in the main radiation path into a reference radiation path, the radiation directed into the reference path having passed through the comb filter but not through the measurement volume, passing the radiation directed into the reference path through a reference volume containing the target gas, detecting the radiation emerging after it has passed through the reference volume and producing a corresponding reference output, an comparing the reference output with the measurement output to produce a signal dependent on the target gas in the measurement volume and substantially independent of any interfering gases.

7. A method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filter having predetermined successive sharp passbands separated by absorbance gaps; repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; producing a measurement output corresponding to the radiation received at the end of the radiation path as the comb filter is shifted whereby the measurement output is a function of the presence of the target gas in the measurement volume; directing some, only, of the radiation in the main radiation path into a reference radiation path after the radiation in the main path has passed through the comb filter but before it has passed into the measurement volume; passing the radiation in the reference path through a reference volume containing a predetermined reference gas having a predetermined absorption characteristic; detecting the radiation after it has passed through the reference volume and producing a corresponding reference output; and using the reference output to correct the measurement output for any changes therein caused by drift in the comb filter.

8. A method according to claim 7, in which the reference output is compared with a predetermined output corresponding to a predetermined drift-free state of the comb filter and any difference resulting from the comparison is used to adjust the comb filter to the predetermined drift-free state.

9. A method according to claim 7, in which the reference gas is the same as the target gas.

10. A method according to claim 7, in which the comb filter is implemented as an etalon having two mirrors the optical spacing between which is variable, and in which the drift in the comb filter comprises variation in the parallelism of the mirrors from exact parallelism and/or variation of the mean optical spacing.

11. A method of detecting the presence of a predetermined target gas having a predetermined pattern of peaks of absorbance to radiation lying within a particular radiation band, the absorbance peaks alternating with absorbance gaps in which the gas transmits at least some of the radiation, comprising the steps of: passing radiation within the said band along a predetermined main radiation path including a comb filter and a measurement volume in which the said gas may be present; the comb filler having predetermined successive sharp passbands separated by absorbance gaps; repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; producing a measurement output corresponding to the radiation received at the end of the radiation path as the comb filter is shifted whereby the measurement output is a function of the presence of the target gas in the measurement volume; storing at least one predetermined reference signal whose variation corresponds to the variation in the measurement output expected in the presence of the target gas in the measurement volume; and comparing the measurement output with the stored signal whereby to determine if the measurement output corresponds to the presence of the target gas in the measurement volume.

12. A method according to claim 11, in which there is a plurality of target gases, and including the steps of storing a plurality of reference signals each corresponding to a respective one of the target gases, and comparing the measurement output with each of the reference signals hereby to determine if the measurement output corresponds to all or any of the target gases.

13. A method according to claim 11, in which said part of the range includes the correlation position.

14. A method according to claim 13, in which the said part of the range includes the anti-correlation position.

15. A method according to claim 13, in which in the correlation position the passbands of the comb filter are aligned with some, only, of the absorbance peaks of the target gas, the excluded absorbance peaks also corresponding to absorption peaks of another gas.

16. A method according to claim 15, in which there is a plurality of target gases, and including the steps of storing a plurality of reference signals each corresponding to a respective one of the target gases, and comparing the measurement output with each of the reference signals whereby to determine if the measurement output corresponds to all or any of the target gases.

17. Apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within said band along a predetermined main radiation path; a comb filter and a measurement volume in said path, the measurement volume being adapted to receive said gas; the comb filter having predetermined successive sharp passbands separated by absorbance gaps; means for repeatedly shifting the passbands of the comb filter, relative to the radiation band over at least part of a range which includes a correlation position in which the passbands substantially coincide with at least some of the absorbance peaks of the gas and an anti-correlation position in which the passbands substantially coincide with at least some of the absorbance gaps of said gas; output means for producing a measurement output corresponding to the radiation received at the end of the radiation path as the comb filter is shifted whereby the measurement output is a function of the presence of the target gas in the measurement volume; and shifting means for shifting the comb filter smoothly and continuously over at least said part of the range, means for producing an electrical output corresponding to the radiation detected during each shift of the passbands, and summing means for summing the level of the electrical output at each of a plurality of predetermined points in each of a predetermined plurality of successive shifts with a corresponding level in the other shifts of that plurality whereby to produce an output signal in which the value dependent on the target gas is increased relative to any value due to noise.

18. Apparatus according to claim 17, in which the shifting means comprises means for shifting the comb filter sinusoidally over at least said part of the range.

19. Apparatus according to claim 17, including means for digitising the electrical output at each of the predetermined points.

20. Apparatus according to claim 17, including means for modulating radiation passed along the predetermined main radiation path at high frequency to produce corresponding modulation in the measurement output, and including means for converting the modulated measurement output to a DC signal and means for digitising the DC signal at the predetermined points during the successive said scans.

21. Apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within said band along a predetermined main radiation path; a comb filter and a measurement volume in said path, the measurement volume being adapted to receive said gas; the comb filter having predetermined successive sharp passbands separated by absorbance gaps; means for repeatedly shifting the passbands of the comb filter, relative to the radiation band over at least part of a range which includes a correlation position in which the passbands substantially coincide with at least some of the absorbance peaks of the gas and an anti-correlation position in which the passbands substantially coincide with at least some of the absorbance gaps of said gas; output means for producing a measurement output corresponding to the radiation received at the end of the radiation path as the comb filter is shifted whereby the measurement output is a function of the presence of the target gas in the measurement volume; and shifting means for shifting the comb filter smoothly and continuously over at least said part of the range, means for directing some, only, of the radiation in the main radiation path into a reference radiation path after the radiation in the main path has passed through the comb filter but before it has passed into the measurement volume, the reference path including a reference volume for containing a predetermined reference gas having a predetermined absorption characteristic, detecting means for detecting the radiation after it has passed through the reference volume and producing a corresponding reference output, and means responsive to the reference output to correct the measurement output for any changes therein caused by drift in the comb filter.

22. Apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within said band along a predetermined main radiation path; a comb filter and a measurement volume in said path, the measurement volume being adapted to receive said gas; the comb filter having predetermined successive sharp passbands separated by absorbance gaps; means for repeatedly shifting the passbands of the comb filter, relative to the radiation band over at least part of a range which includes a correlation position in which the passbands substantially coincide with at least some of the absorbance peaks of the gas and an anti-correlation position in which the passbands substantially coincide with at least some of the absorbance gaps of said gas; output means for producing a measurement output corresponding to the radiation received at the end of the radiation path as the comb filter is shifted whereby the measurement output is a function of the presence of the target gas in the measurement volume; and shifting means for shifting the comb filter smoothly and continuously over at least said part of the range, means for directing some, only of the radiation in the main radiation path into a reference radiation path the radiation directed into the reference path having passed through the comb filter but not through the measurement volume, means for passing the radiation in the reference path through a reference volume containing the target as detecting mean for detecting the radiation emerging after it has passed through the reference volume and producing a corresponding reference output, and comparing means for comparing the reference output with the measurement output to produce a signal dependent o the target gas in the measurement volume and substantially independent of any interfering gases.

23. Apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement volume being adapted to receive the said gas; the comb filter having predetermined successive sharp passbands separated by absorbance gaps; means for repeatedly shifting the passbands of the comb filter, relative to the said radiation band, over at least part of a range which includes a correlation position in which the passbands substantially coincide with at least some of the absorbance peaks of the gas and an anti-correlation position in which the passbands substantially coincide with at least some of the absorbance gaps of the said gas; output means for producing a measurement output corresponding to the radiation received at the end of the radiation path as the passbands of the comb filter are shifted whereby the measurement output is a function of the presence of the target gas in the measurement volume; means for directing some, only, of the radiation in the main radiation path into a reference radiation path after the radiation in the main path has passed through the comb filter but before it has passed into the measurement volume; means for passing the radiation in the reference path through a reference volume containing a predetermined reference gas having a predetermined absorption characteristic; detecting means for detecting the radiation after it has passed through the reference volume and producing a corresponding reference output; and means responsive to the reference output to correct the measurement output for any changes therein caused by drift in the comb filter.

24. Apparatus according to claim 23, including means for comparing the reference output with a predetermined output corresponding to a predetermined drift-free state of the comb filter, and means responsive to any difference resulting from the comparison to adjust the comb filter to the predetermined drift-free state.

25. Apparatus according to claim 23, in which the reference gas is the same as the target gas.

26. Apparatus according to claim 23, in which the comb filter is implemented as an etalon having two mirrors the optical spacing between which is variable, and in which the drift in the comb filter comprises variation in the parallelism of the mirrors from exact parallelism and/or variation of the means optical spacing.

27. Apparatus for detecting the presence of a predetermined target gas having a predetermined pattern of peaks of absorbance to radiation lying within a particular radiation band, the absorbance peaks alternating with absorbance gaps in which the gas transmits at least some of the radiation, comprising: means for passing radiation within the said band along a predetermined main radiation path; a comb filter and a measurement volume in the said path, the measurement volume being adapted to receive the gas; the comb filter having predetermined successive sharp passbands separated by absorbance gaps; means for repeatedly shifting the passbands of the comb filter, relative to the said radiation range, over at least part of a range which includes a correlation position in which the passbands substantially coincide with at least some of the absorbance peaks of the gas and an anti-correlation position in which the passbands substantially coincide with at least some of the absorbance gaps of the said gas; output means for producing a measurement output corresponding to the radiation received at the end of the radiation path as the passbands of the comb filter are shifted whereby the measurement output is a function of the presence of the target gas in the measurement volume; storing means for storing at least one predetermined reference signal whose variation corresponds to the variation in the measurement output expected in the presence of the target gas in the measurement volume; and comparing means for comparing the measurement output with the stored signal whereby to determine if the measurement output corresponds to the presence of the target gas in the measurement volume.

28. Apparatus according to claim 27, in which there is a plurality of target gases and in which the storing means stores a plurality of reference signals e4ach corresponding to a respective one of the target gases the comparing means being operative to compare the measurement output with each of the reference signals whereby to determine if the measurement output corresponds to all or any of the target gases.

29. Apparatus according to claim 27, in which the said part of the range includes the correlation position.

30. Apparatus according to claim 29, in which the said part of the range includes the anti-correlation position.

31. Apparatus according to claim 29, in which in the correlation position the passbands of the comb filter are aligned with some, only, of the absorbance peaks of the target gas, the excluded absorbance peaks also corresponding to absorption peaks of another gas.

32. Apparatus according to claim 23, in which there is a plurality of target gases, and including storing means for storing a plurality of reference signals each corresponding to a respective one of the target gases, and comparing means for comparing the measurement output with each of the reference signals hwereby to determine if the measurement output corresponds to all or any of the target gases.

* * * * *